United States Patent [19]

Barger

[11] 4,029,102

[45] June 14, 1977

[54] CRYOSURGICAL PROBE TIP

[75] Inventor: J. P. Barger, Winchester, Mass.

[73] Assignee: Dynatech Corporation, Burlington, Mass.

[22] Filed: Sept. 9, 1975

[21] Appl. No.: 611,630

[52] U.S. Cl. .............................. 128/303.1
[51] Int. Cl.² ......................... A61B 17/36
[58] Field of Search ................. 128/303.1

[56] References Cited

UNITED STATES PATENTS

| 2,920,790 | 1/1960 | Quenneville et al. | 220/89 A |
| 3,502,081 | 3/1970 | Amoils | 128/303.1 |
| 3,507,283 | 4/1970 | Thomas, Jr. | 128/303.1 |
| 3,788,514 | 1/1974 | Giacoma, Jr. et al. | 220/89 A |
| 3,910,278 | 10/1975 | Crandell et al. | 128/303.1 |

Primary Examiner—Channing L. Pace
Attorney, Agent, or Firm—Cesari and McKenna

[57] ABSTRACT

The spherical welded tip end of a cryosurgical probe is prevented from separating and projecting from the remainder of the probe tip due to fluid pressure in the tip by a lanyard, one end of which is welded to the tip end and the other end of which is secured to a point on the main body of the probe away from the probe tip.

2 Claims, 2 Drawing Figures

CRYOSURGICAL PROBE TIP

BACKGROUND OF THE INVENTION

This invention relates to a cryosurgical probe. It relates more particularly to an improved tip construction for such a probe.

Cryosurgical probes are used to freeze human tissue to effect necrosis, to form scar tissue or to temporarily adhere tissue to the probe tip. These instruments have proved remarkably effective particularly for correcting detached retinas and removing cataracts from the eye.

The tip of the usual pencil-like probe consists of a thin-walled stainless steel tube whose outside diameter is only in the order of 1/16 inch or less. The exposed tip end is closed usually by welding to form a polished spherical surface. That is the working end of the probe which is placed against the tissue.

A small capillary tube extends inside the hollow tip almost to its end and a fluid refrigerant under pressure is supplied to that tube. The fluid expands upon leaving the tube inside the probe tip with the result that the tip end is cooled to a temperature low enough to freeze human tissue.

Conventional pencil-like probes, particularly ophthalmic probes, have an inherent problem which makes some doctors apprehensive about using these instruments. Specifically it has been found that the tip integrity of these probes deteriorates with use. In some cases the deterioration proceeds to the point where the fluid pressure inside the probe tip causes the tip end to separate and project from the rest of the tip. Resultantly, the tip end becomes in effect a small missile which can cause injury to a patient or operating personnel.

The cause of this tip separation is not completely understood. It is believed to be due to physical damage to the tip caused by bending, dents or impacts on the tip. Another possible cause is a chemical reaction between the tip and various impurities which occur if the probe is sterilized by autoclaving without preliminary cleaning. Probe age is another possible factor in the deterioration of probe tip integrity.

Accordingly, it is an object of the present invention to provide a cryosurgical probe whose tip end does not become saparated and project from the probe due to pressurized fluid refrigerant inside the probe tip.

Still another object of the invention is to provide a cryosurgical probe which is safe to use even in delicate eye surgery.

Other objects will in part be obvious and will in part appear hereinafter.

The invention accordingly comprises the features of construction, combination of elements and arrangement of parts which will be exemplified in the following detailed description, and the scope of the invention will be indicated in the claims.

In general, the complete separation and projection of the probe tip end from the remainder of the tip is prevented by a small lanyard, one end of which is welded to the tip end and the other end of which is secured to the main body of the probe at a point spaced appreciably from the probe tip. The lanyard is fairly taut so that if the probe end does separate from the remainder of the tip due to refrigerant pressure inside the tip, the lanyard restrains the tip end so that it cannot be projected from the probe and cause possible injury.

Preferably, the lanyard is a wire which is welded to the spherical tip end as that end is formed so that the inclusion of the lanyard does not materially affect the probe's cost or assembly time. Yet the lanyard should drastically reduce the incidence of injury due to flying tip ends. It should especially relieve the anxiety of doctors who use cryosurgical probes, particularly of ophthalmologist performing delicate eye surgery.

BRIEF DESCRIPTION OF THE DRAWING

For a fuller understanding of the nature and objects of the invention, reference should be had to the following detailed description taken in connection with the accompanying drawing in which.

DESCRIPTION OF THE PREFERRED EMBODIMENT

Figure 1:
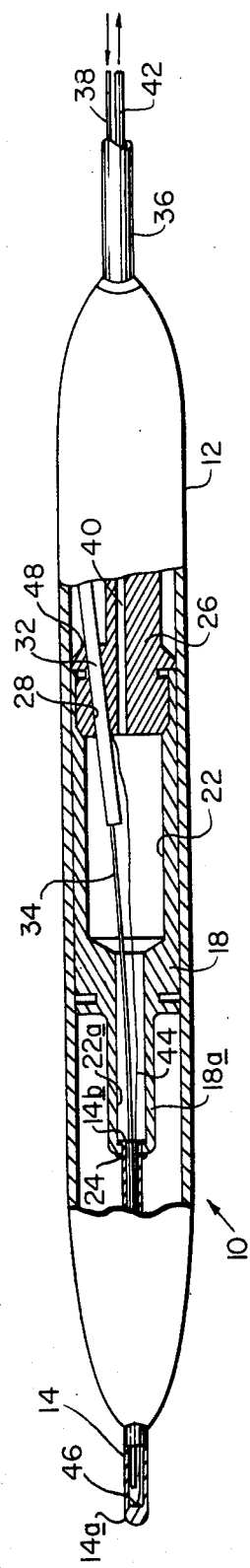
FIG. 1 is a sectional view with parts in elevation showing a cryosurgical probe mode in accordance with this invention.

Turning now to FIG. 1 of the drawing, the probe indicated generally at 10 comprises a generally tubular housing 12 made of a suitable impact-resistant plastic. Projecting from one end of the housing is a tubular probe tip 14 made of stainless steel or other suitable metal. Tip 14 is typically 16 or 17 gauge tubing. The exposed end of the tube is enclosed by a weld to form the tip end 14a which is then polished to a smooth, finished spherical surface.

Housing 12 contains a generally cylindrical barrel 18 having a reduced diameter end 18a extending toward the probe tip. The axial passage 22 in the barrel communicates with a smaller diameter passage 22a extending through the barrel end 18a.

The distal end 14b of the probe tip extends into the end of passage 22a and is flared to help retain it there. Also, a weld bead 24 is formed between barrel end 18a and the wall of tip 14 to securely anchor the tip to the barrel.

A plug 26 extends into open end of passage 22 in barrel 18. A passage 28 extending through plug 26 receives a tube 32 which leads to the barrel passage 22. Tube 32 is connected to a smaller diameter capillary tube 34 which passes through passage 22a and into the tubular tip 14, terminating near its end 14a. Also a flexible sheath 36 extends from the distal end of housing 12. This sheath contains an inlet hose 38 which supplies refrigerant such as nitrous oxide to tube 32. The refrigerant ultimately flows into capillary tube 34 and exhausts from that tube adjacent the tip end 14a.

Upon leaving the tube, the refrigerant expands, cooling in the process, thereby cooling tip 14. Thereupon the refrigerant exhausts through the annular space between the inside wall of tip 14 and tube 34 and thence through passages 22a and 22. The refrigerant leaves the probe through an axial passage 40 in plug 26 and a hose 42 in sheath 36.

In order to insure that the tip end 14a cannot separate completely from the remainder of the tip due to fluid pressure inside the tip 14 and be projected from the probe, the tip end 14a is positively secured to the main body of the probe. More particularly, a lanyard 44 comprising a filament or wire of stainless steel, Constantan alloy or other similarly strong material is connected between the tip end 14a and a plug 26. The lanyard size may typically vary from 0.003 to 0.007 inch depending on the material. One end of this lanyard is securely anchored to tip 14a by a weld 46. The opposite end of the lanyard is threaded through passage 28 in plug 26 as the tube 32 is being installed in that passage and a weld bead 48 is formed between the tube and wire on the one hand and the plug 26 on the other to secure those elements together.

Thus even if the tip end 14a should be fractured, it cannot separate completely from the remainder of the tip and be projected from the probe because the lanyard 44 positively restrains it. In this connection it should be mentioned that for ease of illustration the lanyard 44 is shown as being relatively slack in FIG. 1. In actual practice the lanyard is fairly taut so that it restrains the tip end 14a before that becomes separated appreciably from the main body of the tip.

Figure 2:
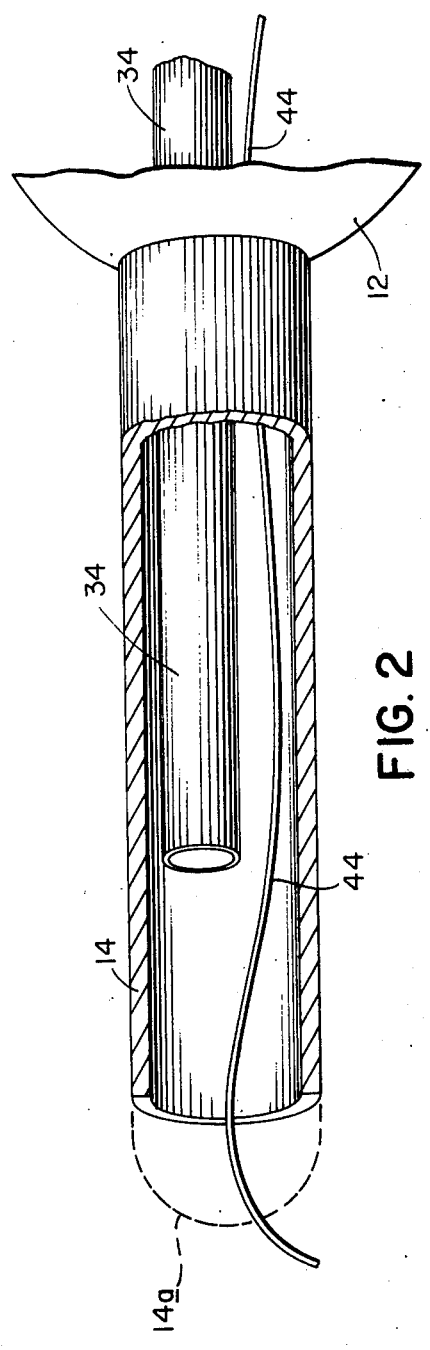
FIG. 2 is a fragmentary sectional view with parts in elevation illustrating a preferred tip construction.

Referring now to FIG. 2, in a preferred probe tip embodiment, the lanyard 44 is anchored to the tip end as the end is being formed. More particularly, before the exposed end of the tube is welded closed to form the finished tip end 14a, the wire lanyard 44 is allowed to project from the end of the tube as indicated in this figure. Then the end of the tube is welded closed as indicated in dotted lines so that the lanyard extends into the weld. Finally the end of the lanyard, if exposed, is severed and the weld finished and polished so that the lanyard end cannot be distinguished from the remainder of the polished tip surface.

This seemingly simple tip construction has alleviated a longfelt problem which as plagued people working with these cryosurgical instruments. Even though this construction does not eliminate the incidence of probe tip end separation, it prevents the tip ends from becoming missiles and therefore should eliminate injuries due to that phenomenon. Yet this new tip construction should not materially increase the cost of the probe or the time required to assemble its various components.

It will thus be seen that the objects set forth above, among those made apparent from the preceding description, are efficiently attained and, since certain changes may be made in the above construction without departing from the scope of the invention, it is intended that all matter contained in the above description or shown in the accompanied drawing be interpreted as illustrative and not in a limiting sense.

It is also to be understood that the following claims are intended to cover all of the generic and specific features of the invention herein described.

I claim:

1. A cryosurgical probe comprising
   A. housing,
   B. a support member inside the housing,
   C. a tubular probe tip having
      1. one end connected to the support member inside the housing,
      2. its opposite end projecting an appreciable distance from the housing, and
      3. for receiving refrigerant under pressure.
   D. means closing the exposed end of the tip to form a tip end having a polished finished exterior surface,
   E. an inextensible lanyard having good tensile strength extending into the probe tip,
   F. means for securing one end of the lanyard directly to the closing means, and
   G. means for securing other end of the lanyard to the support member inside the housing with the lanyard being relatively taut so that if the closing means becomes separated from the tip it cannot be propelled away from the tip by pressurized refrigerant therein.

2. The probe defined in claim 1 wherein the lanyard extends through a passage in the closing means.

* * * * *